United States Patent
Rozenman

(10) Patent No.: US 6,634,753 B1
(45) Date of Patent: Oct. 21, 2003

(54) DISPOSABLE DIAGNOSTIC CONTACT LENS

(75) Inventor: Yaacov Rozenman, Jerusalem (IL)

(73) Assignee: Talia Technology Ltd., D.N. Harei Yehuda (IL)

(*) Notice: Subject to any disclaimer, the term of this patent is extended or adjusted under 35 U.S.C. 154(b) by 0 days.

(21) Appl. No.: 09/937,019

(22) PCT Filed: Mar. 29, 2000

(86) PCT No.: PCT/IL00/00193
§ 371 (c)(1),
(2), (4) Date: Feb. 12, 2002

(87) PCT Pub. No.: WO00/57773
PCT Pub. Date: Oct. 5, 2000

(30) Foreign Application Priority Data

Mar. 29, 1999 (IL) ................................................ 129227

(51) Int. Cl.⁷ .................................................. A61B 3/00
(52) U.S. Cl. ....................................................... 351/219
(58) Field of Search ................................. 351/205, 206, 351/216, 218, 219, 221, 246, 247; 600/452; 606/4

(56) References Cited

U.S. PATENT DOCUMENTS 5,165,409 A  11/1992  Coan

FOREIGN PATENT DOCUMENTS

DE           3032164       4/1981
WO        WO 95 19748     7/1995

*Primary Examiner*—George Manuel
(74) *Attorney, Agent, or Firm*—Lowe Hauptman Gilman & Berner LLP

(57) ABSTRACT

The present invention relates to a sterile disposable and self adaptable diagnostic lens for the purpose of viewing the interior of a patient's eye during a diagnostic examination or during therapeutic procedures. The contact lens is made of a hollow body, having a front (toward eye) and a back (toward physician) exits, filled with transparent flexible material such as a gel. The front exit, facing the eye, is covered by a removable thin film, to keep the gel in place and to keep sterility. The back exit is sealed by a thin transparent window, through which light enters into and comes out of the lens, and can be flat, curved, prismatic or tilted with respect to the main axial axis of the lens. Attaching the front face of the lens to the patient's eye, after removing said film, causes the transparent flexible material outer surface to reshape and fit itself exactly to the patient's eye curvature, thus forming a lens whose curvature negates that of the cornea.

21 Claims, 2 Drawing Sheets

DISPOSABLE DIAGNOSTIC CONTACT LENS

FIELD OF THE INVENTION

The present invention relates to a contact lens for viewing the interior portions of a patient's eye during a diagnostic examination, or a laser treatment, or surgery. More specifically the present invention relates to a sterile disposable lens, made of a hollow body filled with sterile, transparent and flexible material such as a gel.

BACKGROUND OF THE INVENTION

Direct viewing of the internal parts of the eye is impossible because light rays coming from internal parts of the eye either undergo total internal reflection at the cornea/air interface and cannot escape the eye or undergo refraction which focus the rays very close to the cornea. In order for an ophthalmologist to view the interior of a patient's eye, and in particular in order to view the retina or the anterior chamber angle (during routine diagnostic examinations or during laser treatment or surgery), it is necessary to employ a lens that negates the high power of the optical system of the eye.

Many types of ophthalmic diagnostic indirect and contact lenses aimed at this purpose are known. They come in different sizes and shapes, are made of various materials, having different fields of view and are aimed for viewing specific areas of the eye. The diversity of lenses known in the art can be appreciated from the catalogues of well known companies such as Haag Streit, Ocular Instruments, Zeiss, Volk, etc. U.S. Pat. No. 5,165,409 discloses an apparatus for measuring pressure within an eye, the apparatus is capable of providing accurate and reproducible measurements of the intraocular pressure, while permitting the use of disposable sheath for covering the part of the apparatus that touches the eye during measurement. International Publication No. WO 95/19748 discloses a mirrored, hollow lens, filled with a fluid or medium, which reduces the degree of astigmatic focusing which occurs when light or laser light pass through other contact lenses. DE 3032164 discloses an adaptor for use with an objective lens in an ophthalmological microscope comprised of an eyepiece member having an aperture defined therein for containing an impregnating liquid having a refractive index intermediate those of an objective lens and the cornea to be observed and a collar member for supporting the eyepiece member in fixed relation to the objective lens.

Most of the lenses known in the art suffer from a common drawback. They are all designed for multiple-use and between re-uses need to be disinfected or sterilized. It is the practice among persons in the eye care field to posses a limited set of non-disposable lenses that undergo disinfection or sterilization between one patient to another. This practice is in contradiction with the nowadays general trend to employ disposable medical equipment, whenever possible, due to the increasing awareness and demand of both physicians and patients.

Another main drawback common to most of the known diagnostic lenses is the rigid and fixed curvature of their front face (i.e., the face to be facing or contacting the patient's eye) which cannot be fitted exactly to the specific corneal topography of the individual eye under examination. The practice is to make the frontal curvature a bit steeper than the curvature of an average eye and before applying to the eye to put a small amount liquid on the surface which fills the space between the cornea and the lens when applying to the eye. This procedure is somewhat cumbersome and because the front face is made of a rigid material can sometimes results in scratches or erosions to the patient's cornea.

An additional disadvantage common to most lenses stemming from the above, is their high cost caused by the relatively expensive materials from which they are fabricated (high quality glass or plastic) and the great care needed to polish the front face in order to obtain the desired curvature.

It is the aim of the present invention to provide a cheap, easy to handle, disposable and sterile ophthalmic diagnostic lens for use in various eye lens applications such as examining procedures and laser treatments and surgeries.

It is another aim of the present invention to provide a contact lens which, while fulfilling the requirements of sterility and disposability, will have a soft and flexible frontal face such that it will have the ability to adopt itself exactly to the shape of the specific eye under examination, thus providing an optimal lens fit. and at the same time will reduce the risk of injury to eye to a minimum.

SUMMARY OF THE INVENTION

The present invention relates to a sterile disposable and self adaptable diagnostic lens for the purpose of viewing the interior of a patient's eye during a diagnostic examination or during therapeutic procedures such as a laser treatment or a surgery. Said contact lens is made from a hollow body, having a front (toward eye) and a back (toward physician) exits, filled with transparent flexible material such as a gel. The back exit, which serves the physician to illuminate the eye and to look into the eye is sealed by a thin transparent window, through which light enters into and comes out of the lens. The front exit, facing the eye, is covered by a removable thin film, to keep the gel in place and to keep sterility. The back transparent window can be flat, curved, prismatic or tilted with respect to the main axial axis of the lens, or a combination thereof.

Attaching the front face of the lens to the patient's eye, after removing said film, causes the transparent flexible material outer surface to reshape and fit itself exactly to the patient's eye curvature, thus forming a lens whose curvature negates that of the cornea.

The transparent material filling the lens can be cohesive, i.e., leaving no traces of material on the patient's eye or adhesive, i.e. leaving some of the material on the eye, upon removing the lens from the eye at the end of the treatment or surgery.

In a special embodiment of the present invention, the material filling the hollow body is in the form of a dry gel or a powder and a predetermined amount of liquid is added to said dry gel or powder to form the transparent flexible material before the lens is to be used.

In a preferred embodiment of the present invention, the hollow body has a shape of a hollow truncated cone (a cone whose point is cut off) wherein its smaller base is the front circular exit (facing the eye) which is covered by the removable film while the larger one is the back face which serves as an optical surface.

The refraction index of the transparent material can be in the range 1.1 to 1.8.

The combination of the transparent flexible material refractive index and the back window's curvature and thickness is selected according to needs.

According to the present invention the lens can further comprise any optical elements, such as lenses and mirrors, in order to obtain a better and/or magnified image, to reflect the image of peripheral hidden parts of the eye and to increase the field of view.

Keeping the sterility of the lens according to the present invention is achieved by hermetic sterile sealing between the frontal face and the removable film or by packing the whole lens in a hermetic envelope package that keeps sterility.

The so sealed or packed lens undergoes sterilization by any suitable sterilization process known in the art.

BRIEF DESCRIPTION OF THE DRAWINGS

The present invention is further demonstrated and illustrated by FIGS. 1 and 2. These Figures are for the purpose of demonstration and illustration alone and do not limit the scope of the invention in any way.

DETAILED DESCRIPTION OF THE INVENTION

Figure 1A:
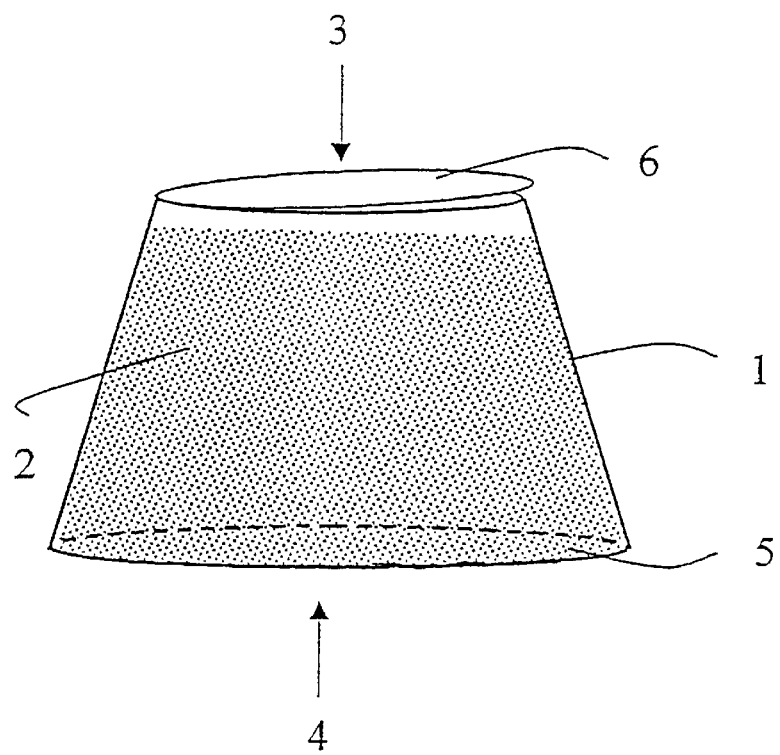
FIG. 1A: The contact lens according to the present invention is made of a hollow body (1) filled with sterile transparent and flexible material (2) and having a front exit (3) and a back exit (4). The front exit, to be attached to the patient's eye is covered with a removable thin film (6). The back exit facing the physician is a transparent window (5). The transparent window (5) can be flat (as in Fig), curved, prismatic or tilted with respect to the plane perpendicular to the main axial axis of the lens, or of a combination thereof.
Figure 1B:
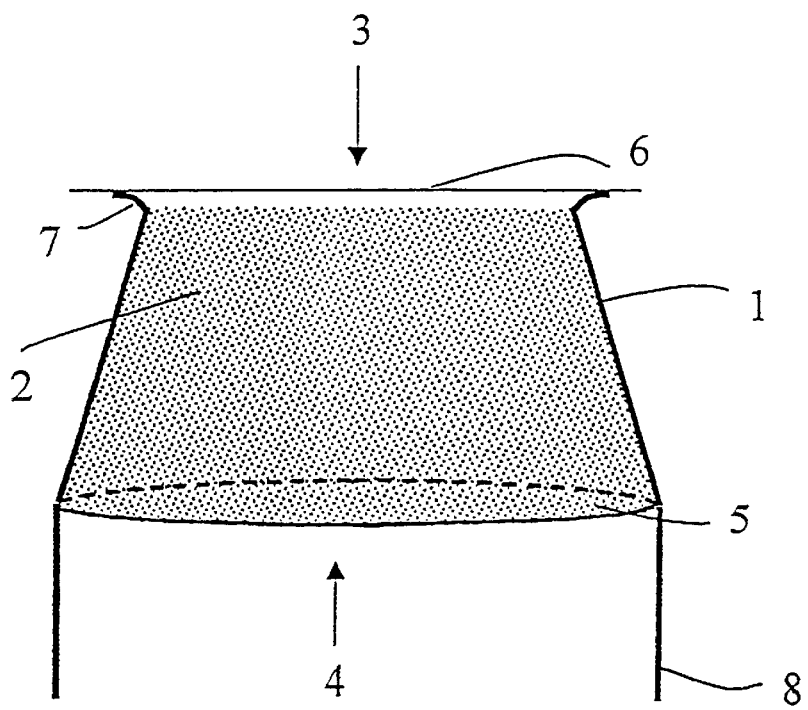
FIG. 1B: The front exit (3) of the hollow body (1) might terminate in a slanted flange (7) having a curvature to fit the cornea, the limbus or the sclera, depending on the lens diameter. The flange can be fabricated from the same material as the main hollow body or from another more flexible material. On its back exit (4) the hollow body can extend (8) beyond the transparent window (5) to enable better holding of the lens.
Figure 2:
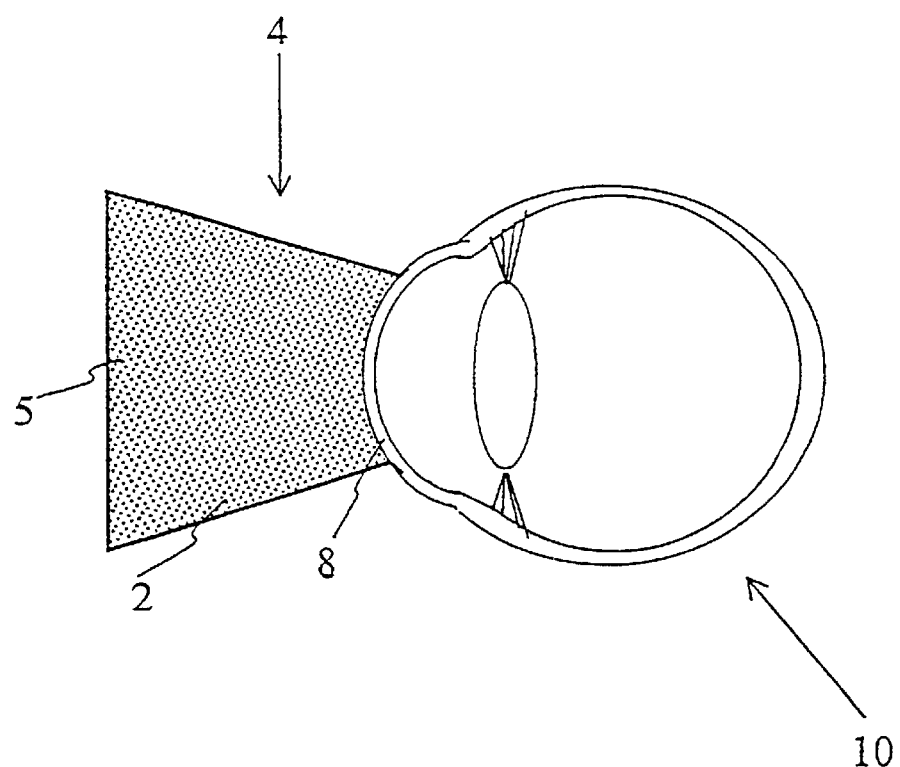
FIG. 2: After removing the removable thin film from the front exit, the lens is attached to the cornea (8) (or the limbus or the bulbar conjunctiva) of the patient eye (10) and the gel (2) adjusts itself to the exact shape of the cornea. The physician views the interior parts of the eye through the transparent window (5). The transparent window (5) can also serve for passing a laser beam into the eye for a laser treatment or a surgery.

The present invention relates to a sterile disposable and self adaptable diagnostic lens for the purpose of viewing the interior of a patient's eye during a diagnostic examination or during therapeutic procedures such as a laser treatment or a surgery. Said contact lens is made from a hollow body, having a front (toward eye) and a back (toward physician) exits and filled with transparent flexible material such as a gel. The back exit, which serves the physician to illuminate the eye and to look into the eye is sealed by a thin, either flat or curved, transparent window, through which light enters into and comes out of the lens. The front exit, facing the eye, is covered by a removable thin film, to keep the gel in place and to keep sterility.

All parts of the lens of the present invention are preferably made of inexpensive materials.

The back transparent window can be flat, curved, prismatic or tilted with respect to the main axial axis of the lens, or a combination thereof.

The transparent flexible material filling the lens, has to fulfill the following requirements: a) it must be approved for medical use; b) it must be soft enough in order not to scratch the eye and in order to adopt itself to the cornea curvature and on the other hand it must be rigid enough in order not to spill out upon removing the removable film.

Said transparent flexible material can be any medical approved gel and in particular any ophthalmic gel known in the art.

Said gel can be selected from various materials among them gels such as: hyaluronic acid, polyacrylic acid, hydroxymethyl cellulose, hydroxypropyl cellulose.

The thickness of the flexible material is preferably in the range 4 to 20 mm.

The transparent material filling the lens can be cohesive, i.e., leaving no traces of material on the patient's eye upon removing the lens from the eye at the end of the treatment or surgery, or adhesive, i.e. leaving some of the material on the eye to form a gel coating on the eye tissue.

In a special embodiment of the present invention, the material filling the hollow body is in the form of a dry gel or powder, such as a gel powder and a predetermined amount of liquid, preferably, distilled water or saline, is added to said dry gel or powder before the lens is to be used. Upon adding the liquid to the dry gel or powder, the material swells to form a transparent flexible gel.

According to this embodiment, the shelf life of the lens can be prolonged while in the case where the flexible material is already in its gel form, the lens' shelf life might be limited due to drying of the gel.

The hollow body can be transparent or opaque, according to needs, and can be fabricated from any inexpensive material such as plastic, glass or metal.

The back transparent window can be made of any transparent material such as glass, plastic, nylon, silicone, or any artificial membrane. It can be fabricated from the same material as the hollow body and be an integral part of it or can be fabricated from a different material. Said window can have a uniform or non-uniform predetermined thickness.

Optionally, the hollow body can extend beyond the back transparent window for better holding. The total length of the lens, including this extension is preferably in the range 1 to 4 cm.

The frontal face can terminate in a slanted flange that can be made of the same or of more flexible material than the main hollow body. Said flange-like termination serves as additional contact surface between lens and eye and can be designed in such a way as to allow maintaining the lens in a fixed position by suction action.

The curvature of said flange is designed to fit the curvature of the cornea, of the limbus or of sclera according to the diameter of the lens' frontal face.

The diameter of the frontal face depends on the desired field of view and preferably is in the range 8–20 mm.

The removable thin film covering the front exit has margins beyond the area of the front exit, to allow convenient peeling of said film from lens immediately before applying the lens to a patient's eye. Said margins can be of any shape, providing it allows convenient gripping. The removable film can be made of any material such as paper, thin plastic film, nylon, silicone film, aluminum foil or any other metal foils.

When the hollow body and the removable film are compatible for hermetic sterile sealing between them, keeping sterility can be achieved by these means. When the hollow body and the removable film are not compatible for hermetic sterile sealing between them, or in addition to these means, the whole lens (including the removable film) can be packed in a sealed hermetic envelope suitable for keeping sterility by any known in the art means for sterile materials and packaging.

The lens according to the present invention can further comprise any optical elements, such as mirrors and lenses, in order to obtain a better and/or magnified image, to reflect the image of peripheral hidden parts of the eye and to increase the field of view.

The transparent flexible material filling the hollow body or the transparent back window, or both, can be colored in order to filter a specific spectral range of the light, according to needs.

What is claimed is:

1. A sterile single-use flexible contact lens for use in viewing the interior of a patient's eye during diagnostic examination or a laser treatment or a surgery, comprising a hollow body (1) having a back (4) and a front (3) exits, filled with a sterile, transparent and flexible material (2), wherein the back exit, facing the physician, is sealed with a thin transparent window (5), and the flexible front exit, to be attached to the patient's eye, is covered by a removable film (6), and said contact lens is characterized in that the removable film keeps the flexible material in place such that after removing the film the front face of the flexible material of the lens can be attached directly to the patients eye causing the flexible material to reshape and fit itself exactly to the patients eye curvature, thus forming a lens whose curvature negates that of the cornea.

2. A sterile single-use flexible contact lens according to claim 1 wherein the transparent flexible material has a refraction index in the range 1.1 to 1.8.

3. A sterile single-use flexible contact lens according to claim 1 wherein the transparent flexible material is cohesive such that no material is left on the eye upon removing the lens from the eye.

4. A sterile single-use flexible contact lens according to claim 1 wherein the transparent flexible material is adhesive such that upon removing the lens from the eye some of said material is left on the eye.

5. A sterile single-use flexible contact lens according to claim 1 wherein the transparent flexible material is any gel approved for medical use.

6. A sterile single-use flexible contact lens according to claim 5 wherein the gel is any ophthalmic gel known in the art.

7. A sterile single-use flexible contact lens according to claim 5 wherein the gel is selected from hyaluronic acid, polyacrylic acid, hydroxymethyl cellulose, or hydroxypropyl cellulose.

8. A sterile single-use flexible sterile disposable contact lens according to claim 7 wherein the powder is a gel powder and the liquid is selected from distilled water or saline.

9. A sterile single-use flexible contact lens according to claim 1 wherein the material filling the hollow body is in the form of a dry gel or a powder and wherein before the lens is to be used, a predetermined amount of liquid is added to said dry gel or powder, and wherein upon adding said liquid to said dry gel or powder, the material swells to form the transparent flexible material.

10. A sterile single-use flexible contact lens according to claim 1 wherein the thin transparent window is either flat, or curved, or prismatic or is tilted with respect to the plane perpendicular to the main axial axis of the lens.

11. A sterile single-use flexible contact lens according to claim 1 wherein the transparent window is having either a uniform or a non-uniform thickness.

12. A sterile single-use flexible contact lens according to claim 1 wherein the transparent window is made of plastic or glass, or nylon or silicone or any other transparent material.

13. A sterile single-use flexible contact lens according to claim 1 wherein the hollow body front exit terminates with a slanted flange, made of the same or of more flexible material than the main hollow body.

14. A sterile single-use flexible contact lens according to claim 1 wherein the hollow body extends beyond the transparent window for better holding.

15. A sterile single-use flexible contact lens according to claim 1 wherein the hollow body is either transparent or opaque.

16. A sterile single-use flexible contact lens according to claim 1 wherein the removable film is made from material selected from paper, nylon, thin plastic film, thin silicone film, aluminum foil or any other metal foil.

17. A sterile single-use flexible contact lens according to claim 1 wherein the removable film is made of material suitable for hermetic sterile packaging and the sealing between said removable film and the frontal exit of the hollow body is a sterile keeping sealing.

18. A sterile single-use flexible contact lens according to claim 1 wherein the whole lens as defined in claim 1, including the removable film, are packed in any packaging suitable for hermetic sterile packaging.

19. A sterile single-use flexible contact lens according to claim 1 further comprising any optical element.

20. A sterile single-use flexible contact lens according to claim 1 further comprising mirrors installed inside the hollow body in order to view peripheral hidden internal parts of the eye.

21. A sterile single-use flexible contact lens according to claim 1 wherein the transparent flexible material or the back transparent window are colored in order to filter the light according to needs.

* * * * *